United States Patent
Meriheinä

(10) Patent No.: US 10,413,233 B2
(45) Date of Patent: *Sep. 17, 2019

(54) MONITORING OF SLEEP PHENOMENA

(71) Applicant: MURATA MANUFACTURING CO., LTD., Nagaokakyo-shi, Kyoto (JP)

(72) Inventor: Ulf Meriheinä, Söderkulla (FI)

(73) Assignee: MURATA MANUFACTURING CO., LTD., Nagaokakyo-Shi, Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/232,258

(22) Filed: Aug. 9, 2016

(65) Prior Publication Data

US 2017/0042471 A1    Feb. 16, 2017

(30) Foreign Application Priority Data

Aug. 10, 2015  (FI) .................................. 20155577

(51) Int. Cl.
*A61B 5/02*    (2006.01)
*A61B 5/00*    (2006.01)
(Continued)

(52) U.S. Cl.
CPC .......... *A61B 5/4818* (2013.01); *A61B 5/0205* (2013.01); *A61B 5/029* (2013.01);
(Continued)

(58) Field of Classification Search
CPC ..... A61B 5/4818; A61B 5/4812; A61B 5/091; A61B 5/7225; A61B 5/029; A61B 5/4806;
(Continued)

(56) References Cited

U.S. PATENT DOCUMENTS 8,128,569 B1* 3/2012 Mason ................. A61B 5/0205
600/484
2005/0177051 A1    8/2005 Almen
(Continued)

FOREIGN PATENT DOCUMENTS

EP    1 146 433 A1    10/2001
EP    1 943 944 A1    7/2008
(Continued)

OTHER PUBLICATIONS

Chung, Gih Sung, et al. "Noninvasive heart rate variability analysis using loadcell-installed bed during sleep." Engineering in Medicine and Biology Society, 2007. EMBS 2007. 29th Annual International Conference of the IEEE. IEEE, 2007.*
(Continued)

*Primary Examiner* — Christian Jang
*Assistant Examiner* — Andrey Shostak
(74) *Attorney, Agent, or Firm* — Squire Patton Boggs (US) LLP

(57) ABSTRACT

The present invention relates to method and a system for detecting sleep phenomena, the phenomena including at least one of sleep cycles and sleep disorders such as sleep apnea and hypopnea. Ballistocardiologic signals are detected from a subject person, which provide simultaneous information on heart rate variability (HVV) and stroke volume (SV) of the subject. Values of parameters reflecting measured characteristics of currently occurring cardiologic and respiration related sleep phenomena are obtained by processing at least said ballistocardiologic signals. Obtained parameters are used for making decisions on detection of said sleep phenomena, and a monitoring result is output in response to detection of a currently occurring sleep phenomenon.

23 Claims, 7 Drawing Sheets

(51) Int. Cl.

| | | |
|---|---|---|
| *A61B 5/0205* | (2006.01) | |
| *A61B 5/024* | (2006.01) | |
| *A61B 5/029* | (2006.01) | |
| *A61B 5/08* | (2006.01) | |
| *A61B 5/11* | (2006.01) | |
| *A61B 5/091* | (2006.01) | |
| *A61B 5/0432* | (2006.01) | |

(52) U.S. Cl.
CPC ........ *A61B 5/02405* (2013.01); *A61B 5/0816* (2013.01); *A61B 5/091* (2013.01); *A61B 5/1102* (2013.01); *A61B 5/4806* (2013.01); *A61B 5/4812* (2013.01); *A61B 5/7225* (2013.01); *A61B 5/024* (2013.01); *A61B 5/02416* (2013.01); *A61B 5/0432* (2013.01); *A61B 5/7203* (2013.01); *A61B 2562/0219* (2013.01)

(58) Field of Classification Search
CPC .......... A61B 5/02405; A61B 5/0205; A61B 5/0816; A61B 5/1102; A61B 5/024; A61B 5/0432; A61B 5/7203; A61B 5/02416; A61B 2562/0219
See application file for complete search history.

(56) References Cited

U.S. PATENT DOCUMENTS

| | | | |
|---|---|---|---|
| 2006/0020295 A1 | 1/2006 | Brockway et al. | |
| 2006/0271108 A1* | 11/2006 | Libbus ............... | A61N 1/36114 607/2 |
| 2008/0033304 A1 | 2/2008 | Dalal et al. | |
| 2008/0051669 A1* | 2/2008 | Meyer ................ | A61B 5/02405 600/484 |
| 2009/0292180 A1* | 11/2009 | Mirow .................. | G16H 10/20 600/301 |
| 2011/0112442 A1* | 5/2011 | Meger .................. | A61B 5/0002 600/595 |
| 2011/0224565 A1* | 9/2011 | Ong ..................... | A61B 5/4824 600/509 |
| 2014/0073890 A1 | 3/2014 | Su et al. | |
| 2015/0112606 A1* | 4/2015 | He .......................... | G06F 21/00 702/19 |
| 2016/0022152 A1* | 1/2016 | Meriheina ............ | A61B 5/0205 600/485 |

FOREIGN PATENT DOCUMENTS

| | | |
|---|---|---|
| EP | 2 292 143 A1 | 3/2011 |
| JP | H11-128186 A | 5/1999 |
| JP | 2012-529334 A | 11/2012 |
| JP | 2012-236083 A | 12/2012 |
| WO | WO 98/43536 A1 | 10/1998 |
| WO | 2007/123923 A2 | 11/2007 |
| WO | 2009/144598 A1 | 12/2009 |
| WO | WO 2010/145009 A1 | 12/2010 |
| WO | 2011/007346 A1 | 1/2011 |
| WO | 2015/061579 A1 | 4/2015 |

OTHER PUBLICATIONS

Finnish Search Report dated Mar. 7, 2016 corresponding to Finnish Patent Application No. 20155577.

Toki Takeda et al., "Time-dependent Sleep Stage Transition Model Based on Heart Rate Variability," 7th Annual International Conference of the IEEE Engineering in Medicine and Biology Society (EMBC), Conference Proceeding Article, pp. 2343-2346, Aug. 25, 2015.

Matteo Migliorini et al., "Automatic Arrhythmia Detection Based on Heart Beat Interval Series Recorded Through Bed Sensors During Sleep," Computing in Cardiology. Conference Proceeding Article. pp. 337-340, Sep. 28, 2011.

Gih Sung Chung et al., "Noninvasive Heart Rate Variability Analysis Using Loadcell-Installed Bed During Sleep," Proceedings of the 29th Annual International Conference of the IEEE Engineering in Medicine and Biology Society, pp. 2357-2360. Aug. 22, 2007.

Ulf Meriheina, "MEMS Accelerometers Target Healthcare Applications", MEMS Technologies, Electronic Engineering Times Europe, Mar. 2013, p. 41.

Juha M. Kortelainen et al., "Sleep Staging Based on Signals Acquired Through Bed Sensor", IEEE Transactions on Information Technology in Biomedicine, vol. 14, No. 3, May 2010, pp. 776-785.

Taous-Meriem Laleg-Kirati et al., "Validation of a Semi-Classical Signal Analysis Method for Stroke Volume Variation Assessment: A Comparison with the PICCO Technique", Annals of Biomedical Engineering, vol. 38, No. 12, Dec. 2010, pp. 3618-3629.

Piotr Przystup et al., "A Multisensor Detector of a Sleep Apnea for Using at Home", HSI 2013 Sopot, Poland, Jun. 6-8, 2013, pp. 513-517.

International Search Report international application No. PCT/IB2016/054663 dated Nov. 21, 2016.

* cited by examiner

MONITORING OF SLEEP PHENOMENA

BACKGROUND

Field

The present invention relates to method for monitoring sleep phenomena. The present invention further relates to a system for monitoring sleep phenomena.

Description of the Related Art

Sleep may be characterized with two major types of sleep: Non-REM (Rapid Eye Movement) sleep and REM sleep, which is also known as dream sleep. Non-REM sleep consists of three stages of sleep having different depth starting from the lightest stage of transition to sleep to a second stage of light sleep, and deepening into third stage of deep sleep, where the sleeper is very difficult to awaken. Sleep occurs in series of recurring sleep stages, where the periods of deep restorative sleep and more alert stages alternate. These periods may be called as sleep cycles.

Sleep apnea (sleep apnoea) is an example of a sleep disorder, characterized by pauses in breathing during sleep. Such pauses may last for seconds or even minutes. When breathing is paused, carbon dioxide builds up in the human body, especially in the blood circulatory system. The brain is signaled to wake the person up by receptors in the blood stream detecting the high carbon dioxide levels, in order to make him/her breathing. Then the person falls asleep again. This kind of incidents may occur several times over the night and reduce significantly the quality of sleep, which may further cause various risks and/or be an important contributor in development of various health problems.

Hypopnea (hypopnoea) refers to another type of a sleep disorder, involving episodes of overly shallow breathing or an abnormally low respiration rate. It's typically defined by a decreased amount of air movement into the lungs, and causes drop of oxygen levels in the blood. Like sleep apnea, sleep is disturbed such that even if persons afflicted with hypopnea may get a full night sleep, they don't feel properly rested.

Ballistocardiography (BCG) is a measure of ballistic forces on the heart. It can be characterized as a mechanical response of the electrocardiographic signal (ECG). As heart pumps blood, two mechanical effects may be measured: motion of the heart causes a recoil effect on the chest, and motion of the blood causes a recoil effect in whole body. A ballistocardiographic (BCG) signal, which may also be called as a ballistocardioglogic signal, has a characteristic form, which is based on the blood flowing up and down in the body. This signal, for example delay and details of the shape of the BCG signal can reveal cardiac dysfunction. So called J-peaks of a BCG signal may be used to measure heart rate (HR) and heart rate variability (HRV) in a similar way as the R-peaks are used in the Electrocardiogram (ECG).

Ballistocardiographic data indicates the extent of mechanical movements of a body that take place in response to the myocardial activity of the heart. Such ballistocardiographic data may then be used to process data that is indicative of heart motion of the subject. Ballistocardiography based on accelerometer(s) or angular rate sensor(s) provides a non-invasive, unobstrusive and relatively lightweight method for measuring both the relative stroke volume of the heart and the beat-to-beat times.

Heart rate variability (HRV) refers to a variation in the beat-to-beat interval of the heart. Although the measured physiological phenomena is the same for HRV and beat-to-beat interval, typical parameters describing these are different. While beat-to-beat time is expressed typically in time scale, heart rate (HR) is typically expressed on a frequency scale, for example in beats per minute. Heart rate variability (HRV) may be expressed through indicating the relative rate change among a number of consecutive beats. Heart rate variability (HRV) may be calculated from detection of beat-to-beat intervals with a suitable data processing function. Variation in the beat-to-beat interval is a physiological phenomenon; the sinoatrial node of the heart receives several different inputs, and the instantaneous heart rate and its variation are results of these inputs. Recent studies have increasingly linked high heart rate variability (HRV) to good health and a high level of fitness, whilst decreased heart rate variability (HRV) is associated to stress and tiredness.

Analysis of heart rate variability (HRV) in the frequency domain is a widely used tool in the investigation of autonomic cardiovascular control. Usually the variability is differentiated in the spectral profile into the high frequency (HF) band (0.10 to 0.40 Hz), the low frequency (LF) band (0.04 to 0.10 Hz), and the very low frequency (VLF) band (<0.04 Hz). For example, breathing cycle causes a natural, clearly detectable variation of heart rate, where the R-R interval on ECG, and the J-J interval in BCG, is shortened during inspiration and prolonged during expiration. This variation is called as Respiratory Sinus Arrhythmia (RSA), which is detected in the high frequency (HF) band. The low frequency (LF) band (0.04 to 0.10 Hz) represents oscillations related to regulation of blood pressure and vasomotor tone including the so-called 0.1 Hz fluctuation. Heart rate variability in the low frequency (LF) band may be referred to as low frequency heart rate variability (LFHRV).

Stroke volume variability (SVV) refers to changes in arterial blood pressure induced by mechanical ventilation. Stroke volume variability (SVV) is a naturally occurring phenomenon in which the arterial pulse pressure falls during inspiration and rises during expiration due to changes in intra-thoracic pressure secondary to negative pressure ventilation (spontaneously breathing). Stroke volume variability (SVV) may be defined as the percentage change between the maximal and minimal stroke volumes (SV) divided by the average of the minimum and maximum over a floating period.

Respiration rate (RR) refers to rate of respiration of a subject. Although it's not a cardiologic measure, respiration rate (RR) may be detected using the same sensor(s) that are used for detecting ballistocardiologic signals, since respiration causes movement of the body of the subject detectable with accelerometer(s) and/or angular rate sensor(s). Respiration rate (RR) may also be obtained indirectly from a stroke volume variation (SVV) signal, since stroke volume (SV) signal amplitude is modulated by respiration.

Patent publication WO2010145009 discloses an apparatus for determining information indicative of physiological condition of a subject. The apparatus comprises an accelerometer sensor device that obtains ballistocardiographic data indicative of heart motion of the subject, measured along a plurality of spatial axes.

Article "MEMS accelerometers target healthcare applications" by Ulf Meriheinä in Electronic Engineering Times Europe, March 2013, pp. 40-41, discloses utilization of relative beat volume variation and beat-to-beat time variation for monitoring recovery state or stress level of a subject.

Various sleep disorders are typically diagnosed in sleep laboratories, using a combination of a variety of measurements, including electroencephalogram (EEG), respiration flow or respiration muscle status, muscle activity and electrocardiogram (ECG). Such measurement setup is complicated and intrusive, thus not practical for longer term or home use. Therefore, there is a need for alternative and easier ways to detect and characterize sleep disorders.

SUMMARY

An object of the present invention is to provide a method and apparatus so as to overcome the prior art disadvantages. Objects of the present invention are achieved with methods and apparatuses as discussed herein.

The present invention is based on the idea of combining analysis of certain characteristics of both heart rate variability (HRV) and stroke volume variability (SVV) obtained simultaneously, so that effects of sleep cycles and stress or tiredness on HRV may be distinguished from those caused by sleep disorders such as apnea or hypopnea, thus enabling both detection of sleep cycles and reliable detection of sleep disorders. The decision making on detection of a sleep condition may further utilize additional information received from the same sensor output signals that are used for detecting the heart rate variability (HRV) and stroke volume (SV) signals, such as respiration rate (RR) or respiration rate variability (RRV).

For detection of sleep disorders such as apnea and hypopnea, the very low frequency heart rate variability (VLFHRV) value and its derivatives may be used. For this, the measured signal may be extrapolated in order to receive output representing the wanted characteristics the low frequency fluctuation. With additional analysis of characteristics of the heart rate variation (HRV) and especially the very low frequency heart rate variation (VLFHRV), sleep disorders may be recognized in more reliable manner, and sleep disorder based changes may be distinguished from for example effects of stress. The low frequency (LF) fluctuations of the heart rate variation (HRV) are particularly useful for analyzing sleep disorders. The very low frequency fluctuations, typically in the range 0.01 ... 0.04 Hz, in the heart rate variation may be extrapolated with calculation of root mean square (rms) value of the VLFHRV, first derivative of the VLFHRV indicating rate of change of the VLFHRV, and optionally using a low pass filter to smoothen the output of said rms and/or rate of change calculations. Although these calculation methods are mathematically simple, they provide useful information for decision making.

For detection of sleep cycles (SC), both high (HFHRV) and low frequency (LFHRV) or very low frequency heart rate variation (VLFHRV) may be used in combination with information on stroke volume variation (SVV). A recovery index may be further calculated by low pass filtering the sleep cycle signal, indicating the level of recovery of the subject during a night.

The present invention provides an advantage that it may utilize non-invasive, unobtrusive signal detection for simultaneously detecting a number of variables providing information on cardiologic and respiratory functions of the subject, which information may be utilized in decision making for detecting sleep phenomena. Such signal detection methods may comprise various known methods for simultaneously obtaining signals representing currently occurring cardiologic and respiratory functions. Preferably, obtained signals comprise electrical signals which may be processed with signal processing devices. In some embodiments, signal detection may comprise ballistocardiologic signal detection and the detected signals comprise a ballistocardiologic signal or signals. In this application, term ballistocardiologic signal refers primarily to an unprocessed signal directly or indirectly detectable from a subject, and term ballistocardiographic signal refers primarily to a signal which is obtained by processing a ballistocardiologic signal. Needed cardiologic and respiratory signals may be obtained simultaneously from a subject using one or more detection devices providing one or more detection signals. According to a specific embodiment, a single detection device may be used to detect a single ballistocardiologic signal, which may be processed for providing all needed ballistocardiographic signals for the detection of the sleep phenomena. Use of ballistocardiologic signal(s) may be specifically beneficial, since they enable obtaining needed signals for detection of the sleep phenomena even without directly touching the subject with the detection device.

According to a first aspect, a method for detecting sleep phenomena is provided. The method comprises simultaneously obtaining a heart rate signal and a stroke volume signal of the heart of a subject, and processing the heart rate signal for obtaining at least one of a low frequency heart rate variability signal and a very low frequency heart rate variability signal. The stroke volume signal is processed for obtaining a stroke volume variability signal, and at least one heart rate variability value is obtained, representing a characteristic of respective one of the obtained low frequency heart rate variability signal and very low frequency heart rate variability signal. A stroke volume variability value is obtained, representing a characteristic of the stroke volume variability signal. The at least one heart rate variability value and said stroke volume variability value are used for detecting a currently occurring sleep phenomenon and a monitoring result is put out in response to detection of the currently occurring sleep phenomenon.

According to a second aspect, the method for detecting sleep phenomena further comprises further processing, by calculating a first derivative of the at least one of low frequency heart rate variability signal and very low frequency heart rate variability signal, for obtaining a rate of change of the respective one of said low frequency heart rate variability signal and very low frequency heart rate variability signal, and using said rate of change of the respective one of the low frequency heart rate variability signal and the very low frequency heart rate variability signal as the heart rate variability value.

According to a third aspect, the method further comprises: further calculating an average value of the rate of change of the respective of the low frequency heart rate variability signal and very low frequency heart rate variability signal over a period of time, and using the average value of the rate of change of the respective of said low frequency heart rate variability signal and very low frequency heart rate variability signal as the heart rate variability value.

According to a fourth aspect, the calculated rate of change or average value of rate of change of the respective one of the low frequency heart rate variability signal and the very low frequency heart rate variability signal is further low pass filtered. Delay effects caused by the post processing are reduced by producing an output signal combining the filtered signal with the output signal at a preceding time period, and the result of post processing the respective signal is used as the heart rate variability value.

According to a fifth aspect, the processing the stroke volume signal comprises at least one of: a) calculating a rms value of said stroke volume signal over a moving or a fixed time window for obtaining the stroke volume variability value, and b) low pass filtering a signal obtained by calculating absolute value of change of stroke volume between two consecutive stroke volume samples for obtaining a low pass filtered stroke volume variability value.

According to a sixth aspect, the method further comprises using the stroke volume variability value for detecting absence of normal or deep breath, and using the absence of normal or deep breath as a discriminating parameter for detection of a sleep phenomenon.

According to a seventh aspect, the method further comprises calculating a respiration rate value indicating respiration rhythm and depth of the subject, and using the respiration rate value for detecting absence of normal or deep breath. Also, the detected absence of normal or deep breath is used as a discriminating parameter for detection of a sleep phenomenon.

According to an eighth aspect, the respiration rate value is calculated based on any one of the stroke volume signal and the stroke volume variability signal.

According to a ninth aspect, the method further comprises producing the stroke volume signal and the heart rate signal by processing at least one ballistocardiologic signal.

According to a tenth aspect, the at least one ballistocardiologic signal is received from a ballistocardiographic device attached to a bed structure.

According to an eleventh aspect, the ballistocardiographic device uses an accelerometer or an angular rate sensor configured to detect a ballistocardiologic signal of the subject.

According to a twelfth aspect, the method is used for detecting a sleep disorder of at least one of sleep apnea and hypopnea. The sleep disorder is recognized by detecting an increase in very low frequency heart rate variability, detecting no significant stroke volume variability, and detecting absence of normal or deep breath.

According to a thirteenth aspect, the method is used for detecting sleep cycles, wherein the sleep cycles are detected from a heart rate variability ratio signal representing ratio of a respiration depth free high frequency heart rate variability value and the low frequency heart rate variability value. The respiration depth free high frequency heart rate variability is obtained by dividing the high frequency heart rate variability value with the stroke volume variability value.

According to a fourteenth aspect, the method further comprises calculating a recovery index by low pass filtering said heart rate variability ratio signal.

According to another aspect, a computer program is provided, the computer program having instructions which, when executed by a computing device or a data-processing system, cause the computing device or the data-processing system to perform the method discussed above.

According to a further aspect, a non-transitory computer-readable memory is provided, comprising instructions for performing, when executed with a computer device or a data-processing system, a method for detecting sleep phenomena. The method comprises simultaneously obtaining a heart rate signal and a stroke volume signal of the heart of a subject, and processing the heart rate signal for obtaining at least one of a low frequency heart rate variability signal and a very low frequency heart rate variability signal. The stroke volume signal is processed for obtaining a stroke volume variability signal and at least one heart rate variability value is obtained representing a characteristic of respective one of the obtained low frequency heart rate variability signal and very low frequency heart rate variability signal. A stroke volume variability value is obtained representing a characteristic of the stroke volume variability signal, and the at least one heart rate variability value and said stroke volume variability value are used for detecting a currently occurring sleep phenomenon.

According to a first system aspect, a system for detecting sleep phenomena is provided comprising detection means configured to simultaneously obtain a heart rate signal of a subject and a stroke volume signal of the subject and processing means configured to process the heart rate signal for obtaining at least one of a low frequency heart rate variability signal and a very low frequency heart rate variability signal. The system comprises interface means for providing a user interface towards a user. The processing means is also configured to process the stroke volume signal for obtaining a stroke volume variability signal, to obtain least one heart rate variability value representing a characteristic of respective one of said low frequency heart rate variability signal and very low frequency heart rate variability signal, and to obtain a stroke volume variability value representing a characteristic of the stroke volume variability signal. The processing means is configured to use the at least one heart rate variability value and the stroke volume variability value for detecting a currently occurring sleep phenomenon. The interface means is configured to output a monitoring result in response to detection of the currently occurring sleep phenomenon.

According to a second system aspect, the processing means is further configured to calculate a first derivative of the at least one of low frequency heart rate variability signal and very low frequency heart rate variability signal, for obtaining a rate of change of the respective one of the low frequency heart rate variability signal and very low frequency heart rate variability signal, and to use the rate of change of respective one of said low frequency heart rate variability signal and the very low frequency heart rate variability signal as the heart rate variability value.

According to a third system aspect, the processing means is further configured to calculate an average value of the rate of change of the respective one of the low frequency heart rate variability signal and the very low frequency heart rate variability signal over a period of time, and to use the average value of the rate of change of the respective one of the low frequency heart rate variability signal and very low frequency heart rate variability signal as the heart rate variability value.

According to a fourth system aspect, the processing means further comprises a low pass filter configured to filter the calculated rate of change or average value of rate of change of the respective one of the low frequency heart rate variability signal and very low frequency heart rate variability signal. Delay effects caused by the filtering on the output signal are reduced by producing an output signal combining the filtered signal with the output signal at a preceding time period. The output signal is used as the heart rate variability value.

According to a fifth system aspect, the processing the stroke volume signal comprises at least one of i) calculating a rms value of the stroke volume signal over a moving or a fixed time window for obtaining the stroke volume variability value, and ii) low pass filtering a signal obtained by calculating absolute value of change of stroke volume between two consecutive stroke volume samples for obtaining a low pass filtered stroke volume variability value.

According to a sixth system aspect, the processing means is configured to use the stroke volume variability value for detecting absence of normal or deep breath, and to use the absence of normal or deep breath as a discriminating parameter for detection of a sleep phenomenon.

According to a seventh system aspect, the processing means is further configured to calculate a respiration rate value indicating respiration rhythm and depth of the subject, and to use the respiration rate value for detecting absence of normal or deep breath, and to use the detected absence of normal or deep breath as a discriminating parameter for detection of a sleep phenomenon.

According to an eighth system aspect, the respiration rate value is calculated based on any one of the stroke volume signal and the stroke volume variability signal.

According to a ninth system aspect, the processing means comprises a device configured to process at least one ballistocardiologic signal for producing the stroke volume signal and the heart rate signal.

According to a tenth system aspect, the detection means comprises a ballistocardiographic device attached to a bed structure.

According to an eleventh system aspect, the ballistocardiographic device comprises an accelerometer or an angular rate sensor configured to detect the ballistocardiologic signal of the subject.

According to a twelfth system aspect, the system is configured to detect a sleep disorder of at least one of sleep apnea or hypopnea. The sleep disorder is recognized by detecting an increase in very low frequency heart rate variability, detecting no significant stroke volume variability, and detecting absence of normal or deep breath.

According to a thirteenth system aspect, the system is configured to detect sleep cycles. The sleep cycles are detected from a heart rate variability ratio signal representing ratio of a respiration depth free high frequency heart rate variability and the low frequency heart rate variability, and the respiration depth free high frequency heart rate variability is obtained by dividing the high frequency heart rate variability value with the stroke volume variability value.

According to a fourteenth system aspect, the processing means is further configured to calculate a recovery index by low pass filtering the heart rate variability ratio signal.

BRIEF DESCRIPTION OF THE DRAWINGS

In the following the invention will be described in greater detail, in connection with preferred embodiments, with reference to the attached drawings, in which.

DETAILED DESCRIPTION

The term computer refers to any electronic device comprising a processor, such as a general-purpose central processing unit (CPU), a specific purpose processor or a microcontroller. A computer is capable of receiving data (data input), of performing a sequence of predetermined operations thereupon, and of producing thereby a result in the form of information or signals (an output). Depending on context, the term computer will mean either a processor in particular or can refer more generally to a processor in association with an assemblage of interrelated elements contained within a single case or housing.

The systems and methods described herein may be embodied by a computer program or a plurality of computer programs, which may exist in a variety of forms both active and inactive in a single computer system or across multiple computer systems. For example, they may exist as software program(s) comprised of program instructions in source code, object code, executable code or other formats for performing some of the steps. Any of the above may be embodied on a computer readable medium, which include storage devices and signals, in compressed or uncompressed form.

As used herein, a computer-readable medium can be any means that can contain, store, communicate, propagate, or transport the program for use by or in connection with the instruction execution system, apparatus or device. The computer readable medium can be, for example but not limited to, an electronic, magnetic, optical, electromagnetic, infrared, or semiconductor system, apparatus, device or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), and optical fiber, and a portable compact disc read-only memory (CDROM).

Figure 1:
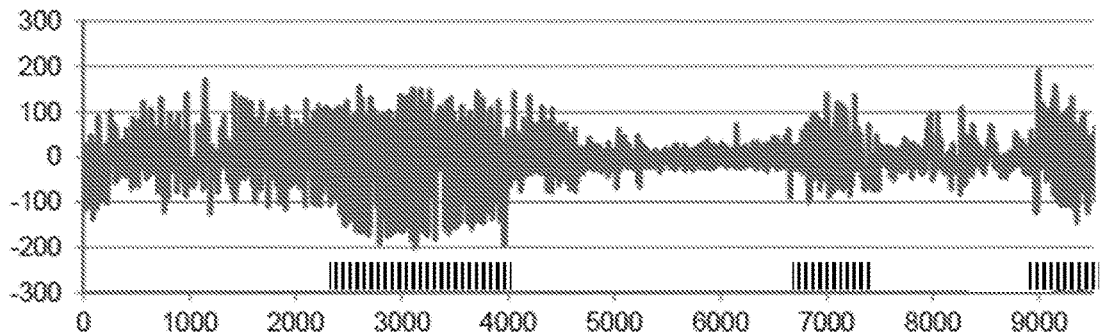
FIG. 1 is an illustration of a very low frequency heart rate variability measured during sleep apnea.

FIG. 1 shows characteristic very low frequency beat-to-beat time fluctuations, also called as very low frequency heart rate variability (VLFHRV) measured during sleep apnea. In this exemplary figure, sleep apnea occurs during time periods about between 0 and 4000 s, and around 7000 s and 9000 s. This is also marked with the striped areas along the horizontal time axis representing time in seconds. Vertical axis in this figure shows high pass filtered beat-to-beat times in milliseconds. Changes to beat-to-beat time fluctuations can be measured with various methods, for example using ballistocardiography (BCG). Alternatively, these measured parameters may be received for example with electrocardiography (ECG), blood pressure measurements with sphygmomanometers, ballistocardiological devices, and pulse wave signal measurements with photoplethysmographs (PPG) or pressure sensors. Characteristics of the low frequency heart rate variability (LFHRV) and very low frequency heart rate variability (VLFHRV) obtained through such measurements may be used to recognize periods of sleep disorder such as sleep apnea in this example, but also other seizures such as epileptic attacks during sleep, and also for recognizing sleep cycles and recovery from stress during sleep, since these different sleep phenomena each have their own characteristic frequency dependencies. Frequency dependencies of these phenomena vary, enabling analysis of such frequency dependencies to be used for recognizing and distinguishing between them. For example, very low frequency heart rate variability (VLFHRV) appears as a dominating characteristic during sleep disorder such as sleep apnea, while low frequency heart rate variation (LFHRV) is more dominant during normal circumstances, and is thus more likely to be advantageous for sleep cycle detection.

Stroke volume, the volume of blood pumped into circulation during each heartbeat, is modulated by the respiration. Thus detection of stoke volume provides a useful method for measurement of respiration depth. Stroke volume variation is a good indicator of detecting normal or deep breathing of a subject. However, the stroke volume variation alone may not be a sufficient measure to detect sleeping disorders such as sleep apnea, since measured stroke volume variation may be affected by person moving or changing position in bed and is influenced by e.g. the blood pressure control. High frequency stroke volume variability caused by modulation of the stoke volume due to respiration may however be used as a discriminating parameter, when analyzing sleep disorders, since both apnea and hypopnea are characterized by a state of the subject where no normal breathing nor deep breathing occurs. The possibility of measuring stroke volume variability in parallel with heart rate variability enables detection of the occurrence of sleep disorders from the measured signal. An accurate sleep disorder indication can thus be obtained directly from one or two sensor data signal inputs with minimal computation. Ballistocardiologic signal is an example of a type of signal that provides opportunity to measure both stroke volume variability and heart rate variability from the same signal. Electrocardiographic signal (ECG) commonly used for detecting functionality of the heart is not useful for stroke volume detection, since it only reflects electrical characteristics of the heart. Ballistocardiologic signal may reflect mechanical movements of the heart and blood, and is thus suitable for detecting both stroke volume and heart rate related parameters.

Figure 2:
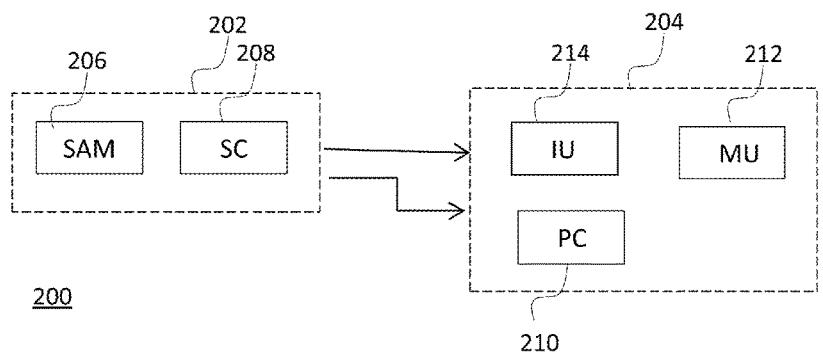
FIG. 2 is a block diagram illustrating functional elements of an embodiment of a monitoring system.

The block diagram of FIG. 2 illustrates functional elements of an embodiment of a monitoring system 200 according to the present invention. The monitoring system 200 gives an example of a configuration that includes a sensor configured to obtain a ballistocardiologic signal that is indicative of both stroke volumes and beat-to-beat times of the of a subject. The monitoring system 200 includes also signal processing means configured to generate from the ballistocardiologic signal measured values of output parameters that are indicative of sleep disorder of the subject. These functional elements may be implemented as one physical device or two or more electrically or communicatively coupled physical devices of the monitoring system 200.

FIG. 2 illustrates an exemplary configuration where the monitoring system (200) comprises a sensor unit (202) and a control unit (204). The sensor unit (202) may be considered as an element to be attached to the monitored subject and the control unit (204) may be considered as an element communicatively coupled to the sensor unit (202) but physically detached from the monitored subject. The sensor unit (202) may be directly attached to or pressing on the monitored subject, or it may be placed to indirectly obtain a ballistocardiologic signal from an element attached to or pressing on the subject, e.g. a bed or a seat. The control unit (204) advantageously comprises circuitry adapted to process signal provided by the sensor unit (202) and circuitry to process data obtained from said signal.

The sensor unit (202) includes one or more sensors (206) for obtaining a ballistocardiologic signal. Ballistocardiology refers in general to a technology for measuring movements of a body, which are caused in response to shifts in the center of the mass of the body during heartbeat cycles. The sensor may sense linear or angular motion of the body and thus be, for example, an accelerometer, or a gyroscope.

The sensor unit (202) may also include a signal processing unit (208) that manipulates the raw electrical input signal to meet requirements of a next stage for further processing. Signal processing may include, for example, isolating, filtering, amplifying, and converting a sensor input signal to a proportional output signal that may be forwarded to another control device or control system. A signal processing unit (208) may also perform some computation functions such as totalization, integration, pulse-width modulation, linearization, and other mathematical operations on a signal. The signal processing unit (208) may alternatively be included in the control unit (204).

In case a sensor of angular motion is used, the sensor unit is advantageously attached to the chest of the subject from which the rotational movement of the heart at every heart beat can be detected and obtained. In linear detection, the sensor unit may be attached directly to the subject, but the sensor unit may alternatively be attached indirectly, for example to a bed where the subject rests in, a mattress in the bed, or the like. An accelerometer may be used to detect the recoil signal of the blood moving in the arteries from the movement transferred to the intermediate item (e.g. the bed or mattress) from the body. Attaching the sensor in the bed enables a very natural sleeping environment, since no sensors or other measurement devices need to be attached to the subject. Thus, the measurement situation itself likely causes less stress on the subject, and the results achieved from the measurement correspond to a natural sleeping situation of the subject.

The control unit (204) is communicatively coupled to the sensor unit to input signals generated by the sensor for further processing. Typically the coupling is electrical, allowing both a power supply to the sensor unit, as well as wireline exchange of signals between the sensor unit and the control unit. The sensor unit may, however, be a standalone unit with its own power supply and radio interface to the control unit. On the other hand, the sensor unit and control unit may be implemented as one integrated physical device.

The control unit (204) is a device that comprises a processing component (210). The processing component (210) is a combination of one or more computing devices for performing systematic execution of operations upon predefined data. The processing component may comprise one or more arithmetic logic units, a number of special registers and control circuits. The processing component may comprise or may be connected to a memory unit (212) that provides a data medium where computer-readable data or programs, or user data can be stored. The memory unit may comprise one or more units of volatile or non-volatile memory, for example EEPROM, ROM, PROM, RAM, DRAM, SRAM, firmware, programmable logic, etc.

The control unit (204) may also comprise, or be connected to an interface unit (214) that comprises at least one input unit for inputting data to the internal processes of the control unit, and at least one output unit for outputting data from the internal processes of the control unit.

If a line interface is applied, the interface unit (214) typically comprises plug-in units acting as a gateway for information delivered to its external connection points and for information fed to the lines connected to its external connection points. If a radio interface is applied, the interface unit (214) typically comprises a radio transceiver unit, which includes a transmitter and a receiver. A transmitter of the radio transceiver unit may receive a bit stream from the processing component (210), and convert it to a radio signal for transmission by an antenna. Correspondingly, the radio signals received by the antenna may be led to a receiver of the radio transceiver unit, which converts the radio signal into a bit stream that is forwarded for further processing to the processing component (210). Different line or radio interfaces may be implemented in one interface unit.

The interface unit (214) may also comprise a user interface with a keypad, a touch screen, a microphone, or equals for inputting data and a screen, a touch screen, a loudspeaker, or equals for outputting data to a user of the device, when triggered by detection of a sleep phenomenon. Data to a user may be used for providing a monitoring result such as displaying or sounding an indicator of detected sleep phenomena by the interface unit (214), or causing an alarm to be initiated on the interface unit (214). In addition to instantaneous presentation of detected sleep phenomena, the interface unit (214) or a memory device attached to it (not shown) may store the data for later display and even further analysis.

The processing component (210) and the interface unit (214) are electrically interconnected to provide means for performing systematic execution of operations on the received and/or stored data according to predefined, essentially programmed processes. These operations comprise the procedures described herein for the control unit of the monitoring system of FIG. 2.

Figure 3:
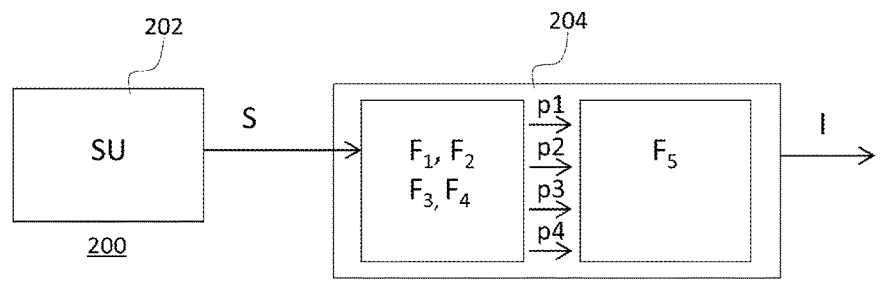
FIG. 3 illustrates functional configuration of the sleep monitoring system.

FIG. 3 illustrates an exemplary functional configuration of the sleep phenomena monitoring system (200) that includes the sensor unit (202) and the control unit (204) of FIG. 2.

The sensor unit, when in direct or indirect contact with the subject, is exposed to the recoil motion of the body during heartbeat cycles. In response to this movement the sensor generates a ballistocardiologic signal (S) and forwards it to the control unit. The control unit includes at least some of processing functions F1, F2, F3 and F4, each of which defines a rule or correspondence between values of the ballistocardiologic signal (S) and values of output parameters (p1, p2, p3) that are indicative of operational parameters of the heart of the subject, and value of output parameter p4 that is indicative of an operational parameter of the respiration of the subject. As known to a person familiar in signal and data processing, the processing functions (F1, F2, F3, F4) may be implemented as separate processing devices or circuitries, such as generic signal and/or data processing devices or application specific processors or circuitries, or in a number of processing devices or circuitries combining at least some of the processing functions (F1, F2, F3, F4) or parts of the processing functions. Any of the processing functions may also be implemented using a combination of more than one processing devices or circuitries. As all parameters (p1, p2, p3, p4) are functions of time, representing physiological characteristics of the subject which are time dependent, the series of temporal values of the parameters (p1, p2, p3, p4) may be considered and handled as signals indicating a specific characteristic of the detected ballistocardiologic signal (S).

In the exemplary embodiment of FIG. 2, the first function (F1) results in values of a first parameter (p1) representing heart rate variability of the heartbeat of the subject. This heart rate variability may be calculated based on the beat-to-beat times obtained from the ballistocardiologic signal, and the frequency range of the calculated variability may be selected by adjusting the first function (F1) so that the variability signal corresponds to the heart rate variability (HRV) at wanted frequencies relevant for the intended measurement. For sleep disorder detection, a low frequency and/or a very low frequency heart rate variability (LFHRV and VLFHRV) signal may be calculated with the first function. The first function (F1) for calculating the low frequency heart rate variability (LFHRV) from the measured beat-to-beat times may comprise several calculation phases, where one or more intermediate results such as an intermediate signal may be obtained which are then used for obtaining the wanted end result. For example, a heart rate (HR) signal may be calculated first based on the measured beat-to-beat times. In one embodiment, the heart rate (HR) signal is low pass filtered so that the high frequency heart rate variability (HFHRV) caused by respiration is excluded from the heart rate (HR) signal, but any lower frequency heart rate variability (HRV) signals such as low frequency heart rate variability (LFHRV), very low frequency heart rate variability (VLFHRV) and even the ultra-low frequency heart rate variability (ULFHRV) are included in the heart rate (HR) signal. Then the wanted low and/or very low frequency heart rate variability (LFHRV and VLFHRV) signals are calculated from the heart rate (HR) signal in the first function (F1) of the control unit (204). The very low frequency heart rate variability (VLFHRV) signal may be presented for instance as variation of the heart rate (HR) signal in milliseconds. Calculation of the low frequency (LFHRV) and/or very low frequency heart rate variability (VLFHRV) may be implemented in various ways, for example by calculation of root-mean-square values of the heart rate (HR) signal over a defined moving or fixed time window, or by filtering the square of the deviation of n consecutive heart rate (HR) signal samples from a low pass filtered average of the heart rate (HR) signal using for example an exponential digital filter.

A second function (F2) of the control unit (204) results in a second parameter (p2) representing another heart rate variability signal (HRV), which includes the high frequency heart rate variability (HFHRV). Providing a heart rate variability (HRV) signal, or the second parameter (p2) representing heart rate variability (HRV) and/or high frequency heart rate variability (HFHRV) may be provided based on the same ballistocardiologic signal (S). The control unit (204) may include a second function (F2), which calculates values for the second parameter (p2) representing high frequency heart rate variability (HFHRV). Calculation of the high frequency heart rate variability (HFHRV) from the ballistocardiologic signal may include for example calculating the absolute value of the change in beat to beat time (BtBt). This change may be calculated for example as the absolute value of difference between two consecutive beat to beat times and by averaging the same over time or low pass filtering it or by calculating the root mean square value of the fluctuation of high pass filtered beat to beat time signal and averaging this value over time of low pass filtering the same.

The third function (F3) results in values of a third parameter (p3) representing stroke volume variability (SVV) of the heart of the subject. The third function (F3) obtaining the stroke volume variability (SVV) may include multiple calculation phases. In one example, a stroke volume (SV) signal is obtained first from the amplitude of the received ballistocardiologic signal, and the variability (SVV) of this signal is then obtained by processing said stroke volume signal. The stroke volume variability (SVV) is typically presented as a relative variability value, comparing for example the absolute value of change ($\Delta$SV) between two consecutively measured stroke volumes (temporal change of stroke volume) to a calculated average stroke volume (SV). The stroke volume variability SVV depends at least on respiration depth. Average stroke volume (SV) may be calculated in many ways, for example obtaining an average value of the stroke volume (SV) over a fixed or a moving time window. The third function (F3) may further or alternatively perform calculation of low pass filtered stroke volume (LPSV), which may be used as an input for sleep disorder detection, since stroke volume of a subject decreases if breathing is weak.

If the control unit is to provide information for sleep disorder detection, it may further comprise a fourth function (F4) which calculates respiration rate (RR) of the subject from the same ballistocardiologic signal (S), and provides a fourth parameter (p4) representing the respiration rate (RR). In an exemplary implementation, respiration rate (RR) is calculated based on the stroke volume (SV) signal as known by a person familiar with the art, as stroke volume (SV) amplitude is modulated by respiration.

The control unit includes also a data processing function (F5) that defines a rule of correspondence between simultaneously measured values of any of the relevant parameters (p1, p2, p3 and/or p4) and at least one value of an output parameter I that indicates detection of at least one sleep phenomenon from the monitored subject. The control unit (204) may store values of the output parameter I to a local data storage for later processing, output it in one or more media forms through the user interface of the control unit, and/or transmit it to a remote node for further processing. The selection of the relevant parameters (p1, p2, p3, p4) to be used in data processing depends on the sleep phenomena to be detected. This selection process will be further described in connection to FIG. 7.

Figure 4:
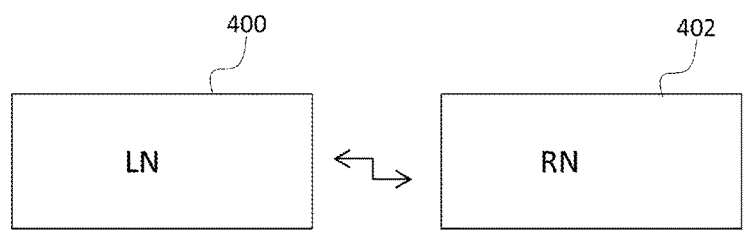
FIG. 4 illustrates a remote monitoring system.

FIG. 4 illustrates a remote monitoring system including the monitoring system of FIG. 2. The system may include a local node 400 that comprises the sensor unit (202) and the control unit (204) of FIG. 2. In addition, the local node (400) may be communicatively connected to a remote node (402).

The remote node (402) may be, for example, an application server that provides a monitoring application as a service to one or more users. One of the aspects monitored with the application may be the level of stress of the user. Alternatively, the remote node may be a personal computing device into which a stress monitoring application has been installed. The local node may be a dedicated device or combination of devices including the sensor unit and the control unit described above. Alternatively, the local node may be implemented as a sensor unit that interfaces a client application in a multipurpose computer device (for example a mobile phone, a portable computing device, or network terminal of a user). A client application in the computer device may further interface the sensor unit and a server application. The server application may be available in a physical remote node (402), or in a cloud of remote nodes accessible through a communication network.

Instead of the above mentioned ballistocardiographic device, a signal that is indicative of both stroke volumes and beat-to-beat times of the heart of a subject can alternatively be obtained with a pulse wave measurement device. Such device comprises a fastening element for detachably attaching a pressure sensor to a position on the outer surface of a subject. The pressure sensor may be configured to generate a pulse wave signal that varies according to deformations of the tissue in response to an arterial pressure wave expanding or contracting a blood vessel underlying the tissue in the position. A processing component is configured to input the pulse wave signal and compute from it pulse wave parameters that represent stroke volumes and beat-to-beat times of the heart of a subject.

Applied sensors are advantageously a microelectromechanical devices, but other detection technologies may be applied, as well. Advantageously a single sensor for measuring both stroke volumes and beat-to-beat intervals is used since it reduces costs and simplifies processing of the two types of parameters.

However, the invention may be implemented also with configurations that generate two separate signals, as long as simultaneous detection is possible.

Figure 5:
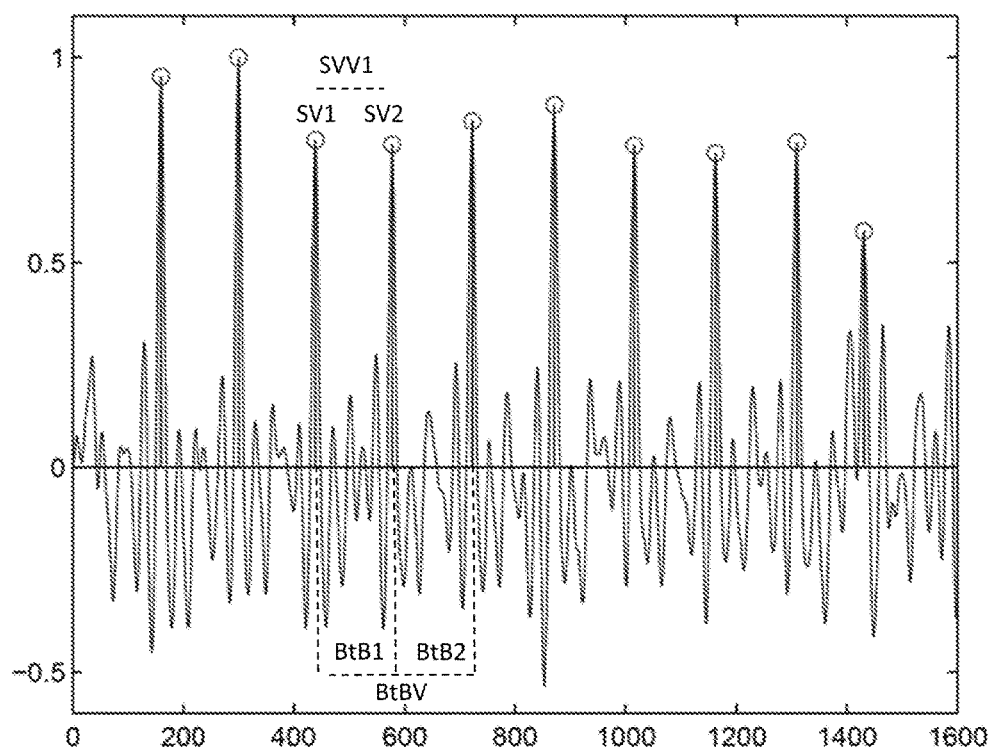
FIG. 5 illustrates an exemplary filtered angular ballistocardiologic signal during heartbeat cycles of a test subject.

Simultaneity in this context is associated to periodic nature of the signal or signals, following the cardiac cycle of the subject. FIG. 5 illustrates an exemplary angular ballistocardiologic signal during heartbeat cycles of a test subject, which may be filtered. The vertical axis represents the magnitude of sensed angular rate in the specific sense direction, and the horizontal axis represents accumulated number of time steps or elapsed time. The control unit may be configured to generate values for various output parameters, for example, a parameter may be indicative of the stroke volume (SVn) of the heart of the subject.

The output parameter for stroke volume may be generated by determining amplitude of the angular ballistocardiologic signal and using that as a value to represent the temporal stroke volume. For example, a peak amplitude, semi-amplitude, or root mean square amplitude may be used for the purpose.

Since the signal is not a pure symmetric periodic wave, amplitude is advantageously measured in respect to a defined reference value, for example, from a zero point of the signal curve. Other reference values may be applied within the scope, as well. Values for stroke volume variability may then be computed as a difference between two successive temporal stroke volume values.

Alternatively, or additionally, a parameter may be indicative of the heartbeat of the subject. For example, the output parameter may be generated by selecting a characteristic point of the angular ballistocardiologic signal (S) and determining the occurrence of the characteristic point in consecutive signal sequences. For example, a minimum or maximum value of the signal sequence may be applied as the characteristic point. The occurrence of the characteristic point may be considered as a time stamp of the heartbeat. A period between two timestamps may be considered to represent temporary beat-to-beat (B-B) time of the heart of the subject, and inverse of this to represent heart rate (HR) of the subject in frequency. Values for beat-to-beat interval variation may thus be computed as a difference between two successive heart rate values.

Similar methods may be used with pulse wave signals; amplitudes of the wave may be applied to determine stroke volumes and periods between characteristic points of successive waves to determine beat-to-beat intervals.

In both the stroke volume variation and the beat-to-beat time variation determination, a specific period of a measured signal is applied. In stroke volume measurements, the amplitude may be determined between a zero point and maximum value at a point of time of the signal curve period. On the other hand, even the whole signal curve period may be applied to compute averaged amplitude values. Partial signal periods between these two examples may be applied as well, depending on the selected amplitude determination mechanism. Beat-to-beat time, or the corresponding heart rate, may be determined from an interval between characteristic points in two successive signal curve periods. Computation of variation of the beat-to-beat times may thus involve two or more successive periods of the signal curve.

Signals including information about beat-to-beat times and stroke volume of a subject are obtained simultaneously and a sleep disorder indication or a sleep cycle indication may be determined as a function of at least the low frequency heart rate variability (LFHRV) and/or the very low frequency heart rate variability (VLFHRV) and the relative stroke volume variability (SVV), both of which can be calculated based on the simultaneously obtained signal(s) as described above. In similar manner, low frequency heart rate variability (LFHRV), high frequency heart rate variability (HFHRV), stroke volume variability (SVV) and even respiration rate (RR) may be calculated based on the simultaneously obtained signal(s) as described above. In this context, the stroke volume signal and beat-to-beat times can be considered to be obtained simultaneously when an interval or intervals applied to determine a value for stroke volume or a value for stroke volume variation and an interval or intervals applied to determine a value for beat-to-beat time for determination of a value for a parameter to be used for sleep phenomena indication at least partly overlap in time. Respiration rate (RR) information may be obtained from the same obtained signal(s), and the respiration rate signal can be considered to be obtained simultaneously with any of the heart rate signal and/or the stroke volume signal, when an interval or intervals applied to determine the respiration rate and the interval or intervals applied to determine a heart rate signal and/or a stroke volume signal at least partially overlap in time.

The concept of simultaneous measurements is illustrated with an example in FIG. 5. FIG. 5 also shows a simplified exemplary computation method where temporal stroke volumes (SV1, SV2) are computed from a difference between a zero point of the signal curve and a maximum point of the signal period. Temporal beat-to-beat times (BtB1, BtB2) are computed from an interval between maximum points of two successive signal periods. Stroke volume variability (SVV1) may be then computed from the difference of temporal stroke volumes (SV1, SV2), and beat-to-beat interval variation BtBV from the difference between temporal beat-to-beat times (BtB1, BtB2).

Intervals applied in this example to determine a value for stroke volume variability and to determine a value for beat-to-beat time variation are marked in FIG. 5 with horizontal dashed lines. It is seen that these intervals at least partly overlap in time and may be applied for determination of a value of sleep disorder indication (SDI) and/or for sleep cycle indication (SCI), which both represent sleep phenomena which may be indicated/detected with the presented principles and processes. Application of this principle to configurations using other signal types or two separate signals is clear to a person skilled in the art.

While it's important to receive quick detection results, delay effects caused by filtering during post processing analysis may be minimized by reversing the time flow and combining the calculated data with the original data for obtaining the sleep phenomena estimate, especially for obtaining the sleep disorder estimate.

An option for a method of obtaining heart rate variability is low pass filtering absolute values of consecutive beat-to-beat time differences. One possible filter function is:

$$y(t)=y(t-1)*(1-k)+k*x(t),$$

where x(t)=ABS(tB2B(t)−tB2Bb(t−1)) and y(t) and y(t−1) are the beat-to-beat times at time steps t and t−1 respectively, and k<1 is a filter coefficient. tB2B(t) and tB2B(t−1) are beat-to-beat times at time steps t and t−1 respectively. The function above indicates that the output signal from this function is a combination of the output signal during the previous time period and the input signal during the current time period.

In order to obtain the very low frequency heart rate variability (VLFHRV) that has been found particularly useful for sleep disorder detection or the low frequency heart rate variability (LFHRV) that has been found to be particularly useful for sleep cycle (SC) detection, the heart rate signal is suitably processed. Useful, yet computationally simple methods for obtaining the very low or low frequency heart rate variability (LFHRV) is to calculate the rms value of the heart rate variability (HR) signal over a suitable moving time window, or by suitably filtering calculated difference between absolute values of two consecutive heart rate (HR) samples. Rate of change (RoC) of the very low (VLFHRV) or low frequency heart rate variability (LFHRV) signal may be obtained by calculating the first derivative of the respective very low (VLFHRV) or low frequency heart rate variability (LFHRV) signal. Alternatively, or in addition, in order to obtain the characteristic signal in the very low frequency area of 0.01 to 0.04 Hz indicating occurrence of sleep apnea, the low frequency heart rate variability signal (LFHRV) may further be filtered.

A low pass filter suitable for this purpose may have a characteristic transfer function such as:

$$y(t)=y(t-1)*(1-k)+k*x(t),$$

where x(t) is the input (calculated LFHRV value) at present time step t, y(t) represents output at time step t and y(t−1) presents output at the previous time step, and k<1 is the filter coefficient. A suitable time step for obtaining a low frequency hear rate variability signal may be for example 1 s or shorter.

An option for a method of calculating the relative stroke volume variability is:

$$SVV(t)=SVV(t-1)*(1-k)+k*x(t)$$

where SVV(t) and SVV(t−1) are the relative stroke volume variability at time steps t and t−1 respectively, k<1 is a filter factor and x(t)=ABS(SV(t)−SV(t−1))/AVE_SV(t), where SV(t) and SV(t−1) are the stroke volume at time steps t and t−1 respectively and AVE_SV(t) is a low pass filtered stroke volume function.

In an embodiment of the invention the ballistocardiologic signal is obtained by an accelerometer or a force or pressure sensor. A heartbeat of a subject results in blood flowing in the body of the subject, resulting in a measurable force.

Derivation of the obtained force signal will result in an acceleration signal. The effect of acceleration caused by the subject moving or from other external sources may be reduced by low pass filtering the obtained acceleration signal to a relevant bandwidth. Both analogue and digital filters may be used, e.g. using function:

$$y(t)=y(t-1)*(1-\bar{k})+k*x(t),$$

where y(t) and y(t−1) are the filter outputs at time steps t and t−1 respectively, x(t) is the filter input at time step t and k is a filter coefficient.

The heartbeat may then be detected by requiring that for a detected heartbeat the filtered function fulfils one or more of the following criteria. The applied criteria compare a sequence of successive maxima and minima to a preset threshold value:

a sequence of three minima and maxima, min1→max1→min2→max2→min3→max3, where the sum of the slopes=(max1−min1)+(max1−min2)+max2−min2)+(max2−min3)+(max3−min3) exceeds a preset limit, a sequence of max→min→max, where the sum of the slopes e.g. =(max1−min2)+(max2−min2) exceeds a preset limit, a sequence of min→max→min, where the sum of the slopes e.g. =(max2−min2)+(max2−min3) exceeds a preset limit.

If one or more of the criteria is fulfilled, a heartbeat is detected. One of the applied maxima or minima (e.g. max1) may be selected as a timestamp of the detected heartbeat. Based on these individual heart beat timestamps, beat-to-beat time intervals and therefrom beat-to-beat time variations may be calculated, as described above.

For further improvement, incorrect time intervals may be removed and missing intervals may be filled in by means of a plausibility criteria. For example:

derived beat-to-beat times shorter than those corresponding to the maximum heart rate of the population, or corresponding to the heart rate of the subject measured, or shorter than those corresponding to the population or the subject under the conditions where the measurement takes place (e.g. sleeping in a bed), are removed, and changes of beat to beat-to-beat times larger than those possible for the population or the subject in question are not accepted.

After use of the plausibility criteria, plausible heart beats remain, and heart rate variation may be accurately calculated, for example, for detection of heart rate variation patterns corresponding to specific sleep disorders or epileptic seizures during sleep.

When needed signals and parameters are available, a decision tree may be utilized for detection of sleeping disorder in order to be able to distinguish characteristics of sleep cycles and/or a sleeping disorder from other physiological circumstances causing change in heart rate variability and/or stroke volume variability. An exemplary flow for processing needed parameters for such decision tree will further be described in connection to FIG. 7.

In order to avoid false positives for sleep disorders, specific discriminator parameters may be utilized. An example of such discriminator parameter is for instance the stroke volume variability (SVV). Another useful discriminator parameter is the respiration rate (RR). Analysis of the earlier mentioned low frequency heart rate variability (LF-HRV) related parameters provide indication of sleep disorder such as sleep apnea, when combined with absence of normal or deep respiration, which may be detected from the stroke volume variability (SVV) signal or obtained from a respiration rate (RR) signal or obtained as a respiration rate irregularity (RRI) signal, which is a derivative of the respiration rate (RR) signal. Alternative or additional discriminator parameters may be for example basic frequency of the very low frequency heart rate variation (VLFHRV), which should be in the range of 0.01 . . . 0.04 Hz, or measurement of blood oxygen saturation (SPO2).

Figure 6:
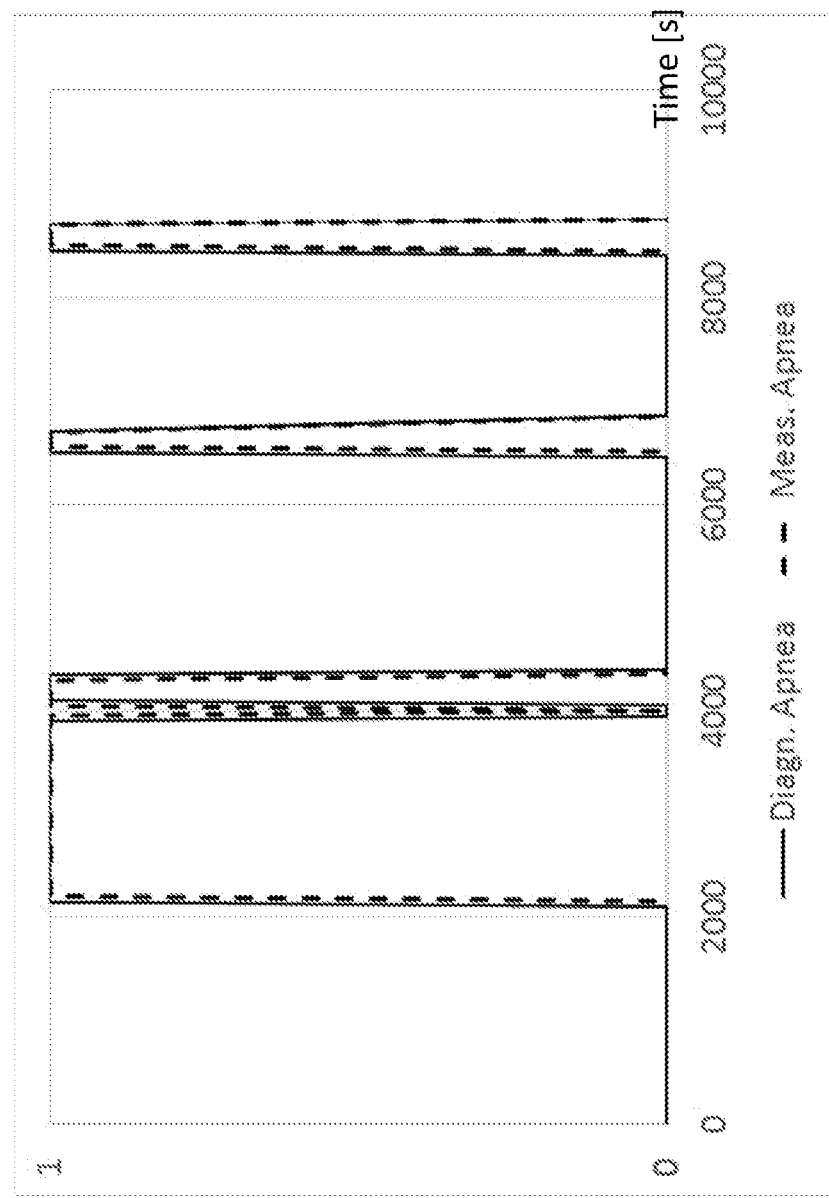
FIG. 6 illustrates result of sleep disorder detection.

FIG. 6 illustrates a result of sleep disorder monitoring based on measured fluctuation of low frequency heart rate variability (LFHRV) shown in FIG. 1 combined with information on stroke volume variation (SVV) with a decision tree described above. It can be seen that in combination result of the analysis of the parameters indicating measured/detected apnea (Meas. Apnea), marked with a dashed line has a high correlation with actual diagnosed apnea (Diagn. Apnea) marked with a solid line, wherein the diagnosed apnea result is received with a combination of more complicated clinical measures. This graph clearly shows the capability of the presented measurement system for detecting sleep disorders non-invasively, unobtrusively and with high accuracy.

One option is that the monitoring system is configured to be applied with the bed to monitor the subject. The monitoring system may thus include one or more separate elements fixedly or detachably coupled to the bed, or included as an integral part of the bed. Embodiments of the invention thus include also a bed that includes at least part of the elements of the monitoring system.

For example, it has been detected that recoil of the body to the heartbeat of the subject tends to vibrate the bed in the longitudinal direction. This vibration may be detected in 0.5 . . . 3 Hz frequency band—typically about 60 beats per minute—with an advanced inclinometer. The sensor used in the bed may preferably be a low noise sensor, with a low noise density, which should preferably be below 20 µg/√Hz (g stands for the Earth's standard acceleration due to gravity) for achieving adequate signal to noise ratio in a typical bed. A sensor like this can detect a ballistocardiologic signal, and also changes in inclinations of merely fractions of degrees of an angle. The amplitude of the vibration is of the order of ~1 mg (g=Earth's standard acceleration), and typically the ballistocardiologic signal of the vibration requires amplification before further analog-to-digital conversion. The same sensor may be used to detect longitudinal and/or transverse inclinations caused by movements of the subject. Typically the motion signal is not amplified in order to avoid saturation.

Figure 7:
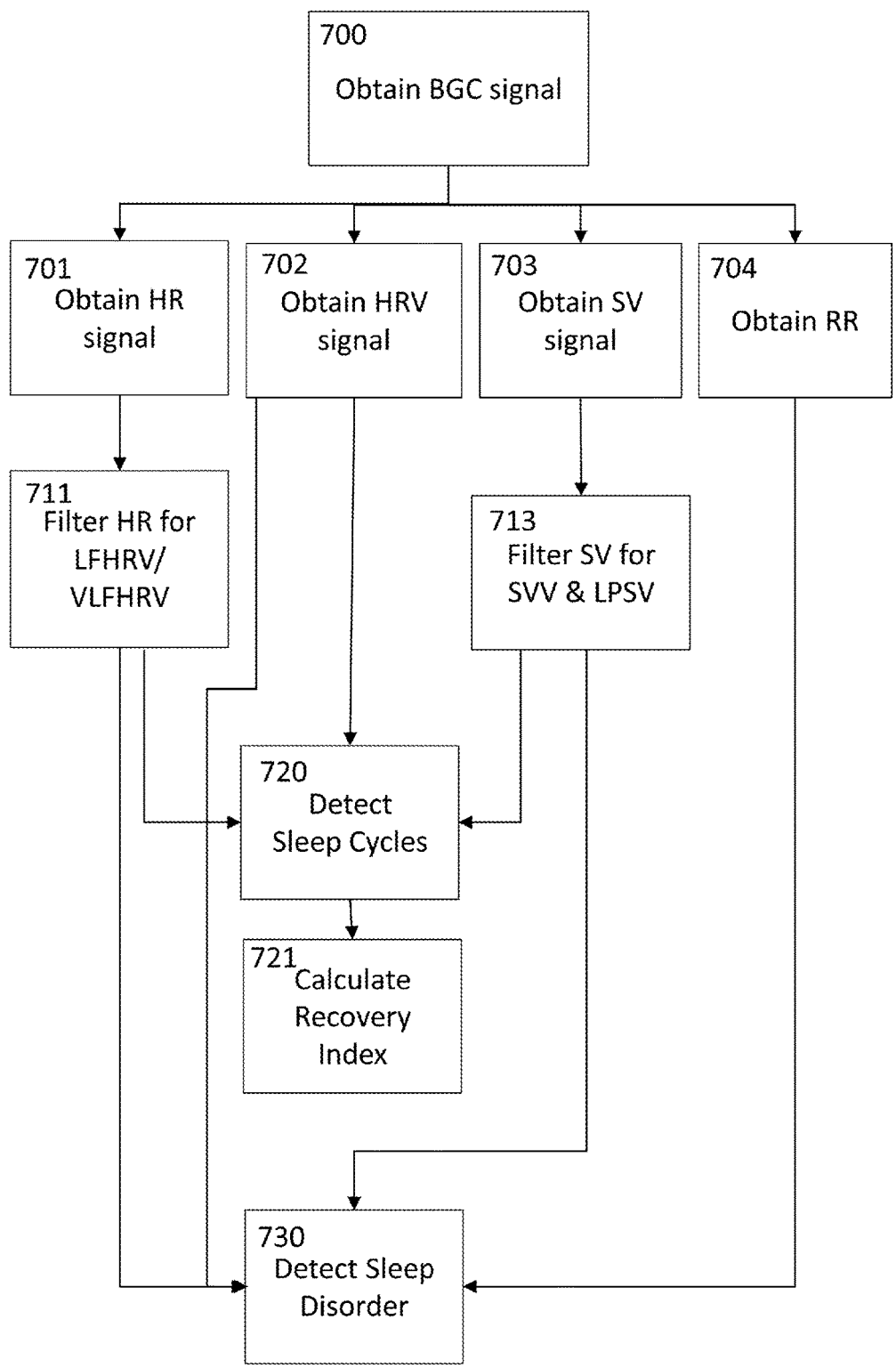
FIG. 7 illustrates an exemplary process flow for recognizing sleep cycles and sleep disorders from the detected ballistocardiologic signal.

FIG. 7 illustrates an exemplary process flow for obtaining parameters for decision making for recognizing sleep cycles and sleep disorders from the detected ballistocardiologic signal (S).

In phase 700, the ballistocardiologic signal (S) is obtained using the sensor device(s). This signal is then processed in several phases (701, 702, 703, 704) which may preferably occur parallel.

In phase 701, instantaneous heart rate information is obtained from the ballistocardiologic signal (S). This heart rate (HR) information may be considered as a being a signal, which may be further processed. This heart rate (HR) signal preferably include at least some of a low frequency (LF-HRV), a very low frequency (VLFHRV) and an ultra-low frequency (ULFHRV) heart rate variability information. This heart rate (HR) signal is further low pass filtered in phase 711 for obtaining value of the very low frequency heart rate variation (VLFHRV) parameter or used as such or high pass filtered low frequency heart rate variation (LF-HRV) parameter. Alternatively, a band pass filter may be used for filtering the heart rate (HR) signal, depending on the heart rate frequencies included in the heart rate signal (HR) and the wanted heart rate (HR) related output parameter (LFHRV, VLFHRV). The parameter may be obtained with the first function (F1) described in connection to FIG. 3.

In phase 702, heart rate variation (HRV) information is obtained from the ballistocardiologic signal (S). This heart rate variation (HRV) information may be considered as a signal representing at least high frequency heart rate variation (HFHRV), and value(s) of the high frequency heart rate variation (HRHRV) parameter is obtained based on this signal. Value(s) of the high frequency heart rate variation (HFHRV) parameter may be obtained with the second function (F2) described in connection to FIG. 3.

In phase 703, stroke volume (SV) information is obtained from the ballistocardiologic signal (S). This stroke volume (SV) information may be considered as a signal including information on stroke volume variation (SVV). The stroke volume (SV) signal may further be processed in phase 713 by a low pass filter in order to obtain value(s) of stroke volume variation (SVV) parameter, and/or by a high pass filter in order to obtain value(s) of a low pass filtered stroke volume (LPSV) parameter. Stroke volume variation (SVV) parameter and/or the low pas filtered stroke volume (LPSV)

parameter may be obtained with the third function (F3) described in connection to FIG. 3.

In phase 704, respiration rate (RR) information is obtained from the ballistocardiologic signal (S) and a parameter is obtained representing the respiration rate (RR). This parameter may be obtained with the fourth function (F4) described in connection to FIG. 3. In an alternative implementation, respiration rate (RR) parameter may be obtained by processing the stroke volume (SV) signal.

For sleep cycle (SC) detection, the values of very low frequency heart rate variability (VHFHRV), the high frequency heart rate variability (HFHRV) and the stroke volume variability (SVV) parameters obtained in phases 711, 702 and 713 are analyzed in phase 720. The sleep cycle (SC) detection process may further comprise low pass filtering a function of the parameters.

In sleep cycle (SC) detection, a further data processing phase (721) may be included for calculating a recovery index (RI) value, which represents the magnitude of recovery over a whole detected night sleep. While sleep cycle (SC) is a complicated curve which may be fully analyzed only by an expert, a simplified recovery index (RI) may be a useful indicator for a person utilizing a sleep phenomena detection system like the one presented here for detecting sufficiency of recovery. Such information may be useful for instance for a sportsman who wishes to monitor for optimal training and for avoiding overtraining, or for monitoring people with sleep problems related to physical or mental issues.

For sleep disorder detection, obtained values of very low frequency heart rate variation (VHFHRV), high frequency heart rate variation (HFHRV), low pass filtered stroke volume (LPSV), respiration rate (RR) and heart rate (HR) parameters may be used as variables in the decision tree for making decision on whether a sleep disorder such as sleep apnea or hypopnea has occurred during the current detection period. Probability of sleep apnea is increased if:
  very low frequency heart rate variation (VLFHRV) has increased, i.e. heart rate (HR) oscillates at a typical frequency of about 0.01 . . . 0.04 Hz;
  high frequency heart rate variation (HFHRV) and/or stroke volume variation (SVV) parameter values show no significant variation, indicating absence of normal or deep breath;
  low pass filtered stroke volume (LPSV) shows a decrease, indicating that average stroke volume has decreased from a reference value and/or has a decreasing trend;
  no normal measured respiration rate (RR) signal is detected, indicating very low (apnea) or very high (hypopnea) respiration rate (RR); and
  heart rate (HR) change has a positive trend—heart rate appears to increase.

Reference levels or reference values of any of above values are normal values of the respective characteristics detected and/or expected to be detected from the subject during normal sleep cycle without sleep disorder. A subset of above characteristics described above may be sufficient for sleep disorder detection, but reliability of correct detection likely increases when more criteria is used for decision making. In an exemplary configuration, very low frequency heart rate variation (VLFHRV) and stroke volume variation (SVV) may be sufficient for detecting a sleep disorder, when combined with information on absence of normal or deep breath, which may be detected from the respiration rate (RR), which may be obtained from the stroke volume variation (SVV) signal. In another embodiment, absence of normal or deep breath is detected from high frequency heart rate variation (HFHRV) signal. The exact structure of the decision tree may vary according to parameters used as decision making criteria, as known by a person familiar with the art.

Figure 8:
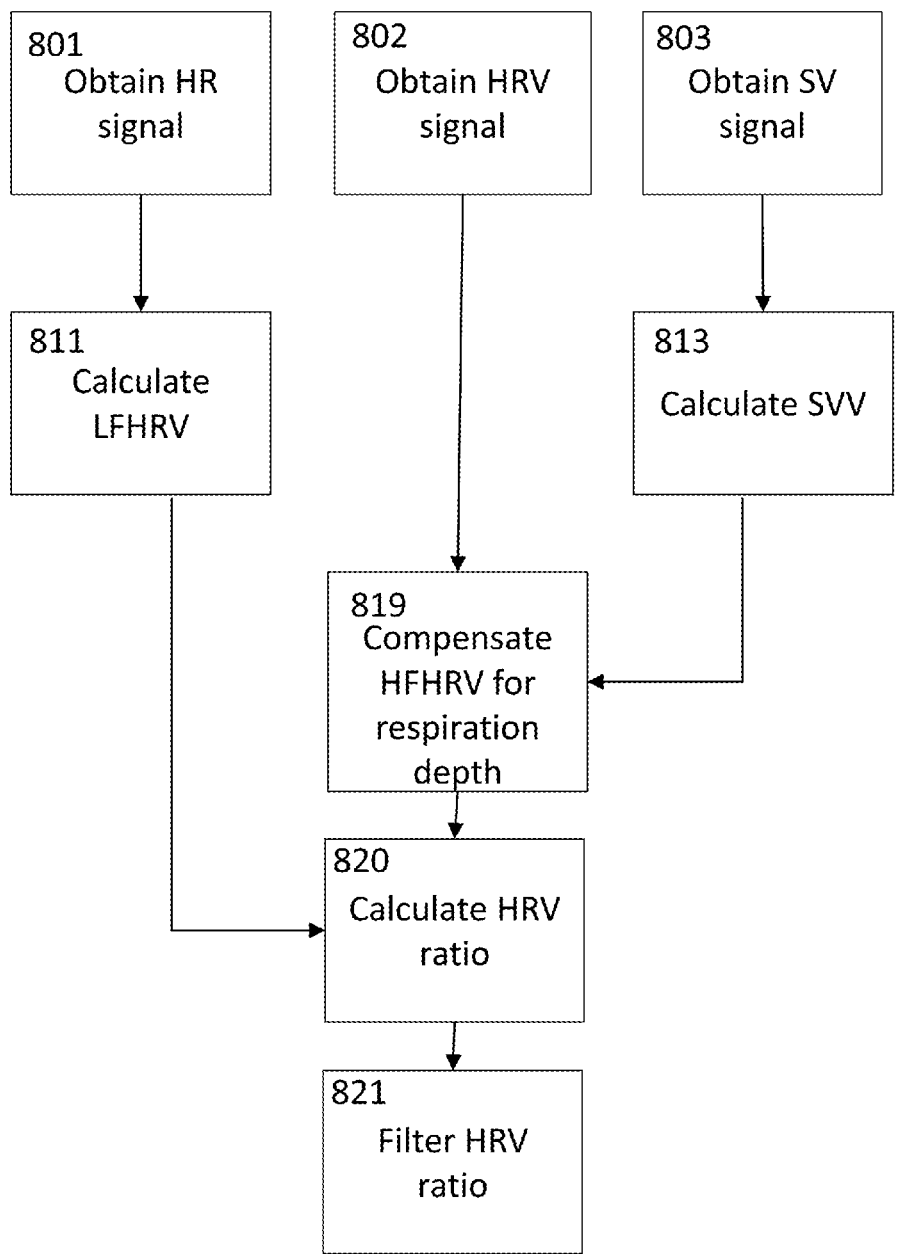
FIG. 8 illustrates more in detail an exemplary process flow of detecting sleep cycles.

FIG. 8 illustrates an exemplary process for determining sleep cycles.

Extraction of sleep cycle (SC) information utilizes same basic signals as described earlier, namely the heart rate (HR) signal, the heart rate variation (HRV) signal and the stroke volume (SV) signal, which are obtained in phases 801, 802 and 803, respectively.

Heart rate (HR) signal is processed in phase 811 for calculating low frequency heart rate variability (LFHRV). This calculation may comprise filtering the heart rate (HR) signal in order to extract the variability in the wanted, characteristic low frequency area.

Stroke volume (SV) signal is processed in phase 813 for calculating stroke volume variability (SVV) which is proportional to respiration depth. This calculation may be expressed for example with equation:

$$SVV = \Delta SV/SV$$

Heart rate variability signal (HRV) includes the high frequency heart rate variability, which is mainly modulated by respiration. In phase 819, the heart rate variability (HRV) signal is compensated for the effect of respiration depth, in order to obtain a respiration depth free high frequency heart rate variation (HFHRV) signal. This compensation may be implemented by utilizing respiration depth information contained in the stroke volume variation signal (SVV). For example, a ratio of the high frequency heart rate variation (HFHRV) signal and stroke volume variation (SVV) signal may be calculated for obtaining a respiration depth free high frequency heart rate variability (RF-HFHRV). Other calculation methods may be used for obtaining the respiration depth free high frequency heart rate variability (RF-HF-HRV) without departing from the scope.

In phase 820, a heart rate variability (HRV) ratio is calculated, representing ratio of the respiration depth free high frequency heart rate variability (RF-HFHRV) and the low frequency heart rate variability (LFHRV). This ratio describes the sleep cycle phase, and gives an indication of stress & recovery status. This ratio may be called as the sleep cycle indicator (SCI). An example of an applied function to calculate the sleep cycle indicator (SCI) may be:

$$SCI = (HRHRV/SVV)/LFHRV$$

The heart rate variability (HRV) ratio calculated in phase 820 may further be filtered in order to remove noise from the signal. Instead of the result of phase 820, the result of this filtering may also be called as the sleep cycle indicator (SCI).

Figure 9:
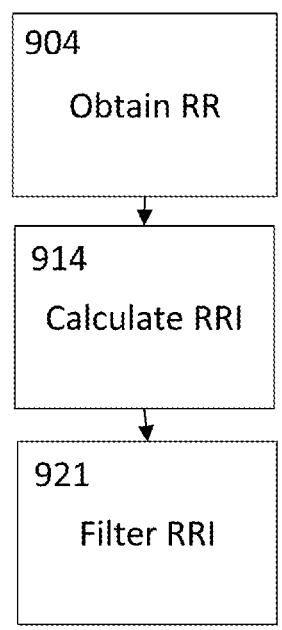
FIG. 9 illustrates calculation of a respiration rate irregularity.

FIG. 9 illustrates calculation of a respiration rate irregularity (RRI), which may be used as a further parameter for indicating sleep stage, since irregularity in respiration rate is one characteristic of sleep depth.

Respiration rate (RR) is obtained in phase 904 in similar manner as described in connection to FIG. 7. For example, the respiration rate may be extracted from the ballistocardiologic signal (S), or from the stroke volume (SV) signal or its derivatives such as stroke volume variability (SVV) signal.

In phase 914, a respiration rate irregularity (RRI) is calculated, representing variability of the respiration rate. Calculation of the variation of the respiration rate (RR) may be calculated as variation of a parameter as known to a person familiar with the art. This respiration rate irregularity (RRI) may be utilized as an additional indicator of the sleep stage. An optional filtering phase 921 may be further utilized to remove noise from the respiration rate irregularity (RRI) signal.

Figure 10:
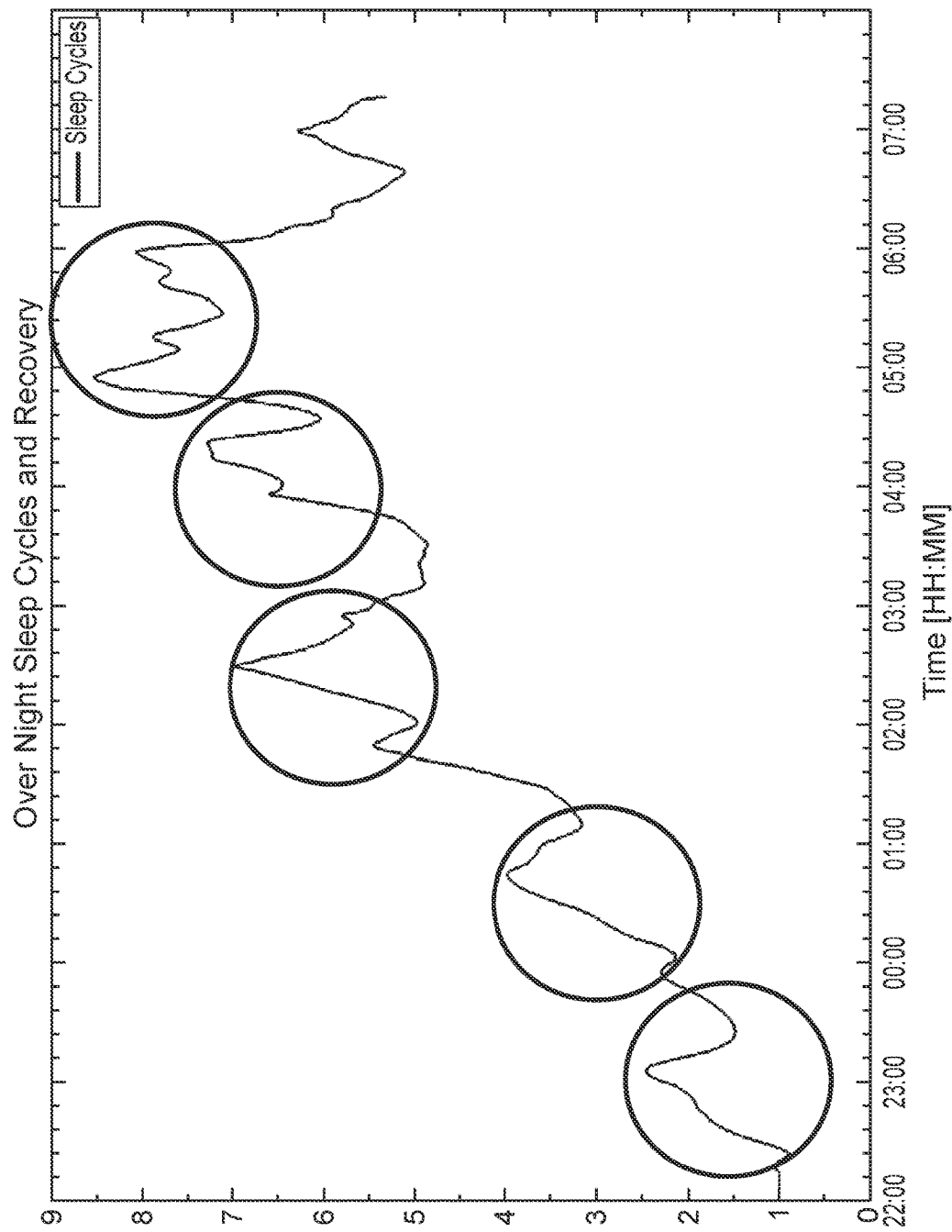
FIG. 10 illustrates a signal representing sleep cycles.

FIG. 10 illustrates a signal correlating with sleep cycle, such as the sleep cycle indicator (SCI), measured from a real subject, which may be displayed on a display unit. It may be noticed, that the curve has a rising trend, indicating recovery of the subject during the night, which reflects for example the increase in the stroke volume variability (SVV). Recovery shows as a rising trend of the sleep cycle indicator (SCI). During the first hours of sleep, the heart rate variability (HRV) and thus also sleep cycle indicator (SCI) is relatively low, indicating that the subject is stressed or tired, and by morning, the heart rate variability (HRV) and thus also the sleep cycle indicator (SCI) gains significantly higher values, which can be noticed from the level change of the sleep cycle indicator (SCI) value between consecutive sleep cycles, and the subject wakes up in the morning well rested. Approximate locations of consecutive sleep cycle periods have been highlighted with circles.

It is noted that the invention or its embodiments are not limited to any specific sensor type or to any number of sensors. One or more sensors can be used separately or in combination in the means for obtaining the needed heart rate (HR) or beat-to-beat time (BtBt) and stroke volume (SV) signals.

It is apparent to a person skilled in the art that as technology advanced, the basic idea of the invention can be implemented in various ways. The invention and its embodiments are therefore not restricted to the above examples, but they may vary within the scope of the claims.

The invention claimed is:

1. A method for monitoring sleep disorders, said method comprising:
    obtaining a ballistocardiologic signal of a subject with a ballistocardiographic device;
    processing said ballistocardiologic signal with a processing device for obtaining simultaneously a stroke volume variability signal, a high frequency heart rate variability signal, a very low frequency heart rate variability signal, and a low frequency heart rate variability signal;
    obtaining with the processing device a low frequency heart rate variability value representing a characteristic of the low frequency heart rate variability signal;
    obtaining with the processing device a very low frequency heart rate variability value representing a characteristic of the very low frequency heart rate variability signal;
    obtaining with the processing device a stroke volume variability value representing a characteristic of the stroke volume variability signal;
    obtaining with the processing device a high frequency heart rate variability value representing a characteristic of the high frequency heart rate variability signal;
    obtaining with the processing device a respiration depth free high frequency heart rate variability value by dividing the high frequency heart rate variability value with the stroke volume variability value;
    obtaining with the processing device a heart rate variability ratio by dividing the respiration depth free high frequency heart rate variability value with the low frequency heart rate variability value;
    detecting with the processing device a currently occurring sleep phenomenon using said heart rate variability ratio;
    detecting in the processing device a sleep disorder if the very low frequency heart rate variability value during the detected sleep phenomenon is higher than a predefined reference value; and
    outputting through an interface unit an indication of the detected sleep disorder.

2. The method according to claim 1, further comprising:
    further processing, by calculating a first derivative of at least one of the low frequency heart rate variability signal and the very low frequency heart rate variability signal, for obtaining a rate of change of the respective one of said low frequency heart rate variability signal and said very low frequency heart rate variability signal; and
    using said rate of change of said respective one of said low frequency heart rate variability signal and said very low frequency heart rate variability signal as the respective one of the low frequency heart rate variability value and the very low frequency heart rate variability value.

3. The method according to claim 1, further comprising:
    further calculating an average value of a rate of change of the respective said low frequency heart rate variability signal and very low frequency heart rate variability signal over a period of time; and
    using said average value of the rate of change of the respective of said low frequency heart rate variability signal and very low frequency heart rate variability signal as the respective one of the low frequency heart rate variability value and the very low frequency variability value.

4. The method according to claim 2, wherein the calculated rate of change or an average value of rate of change of the respective one of said low frequency heart rate variability signal and said very low frequency heart rate variability signal is further low pass filtered, wherein delay effects caused by said low pass filtering are reduced by producing an output signal combining the filtered signal with the output signal at a preceding time period, and wherein a resulting combined signal is used as the respective one of the low frequency heart rate variability value and the very low frequency heart rate variability value.

5. The method according to claim 1, wherein said obtaining said stroke volume variability value further comprises at least one of:
    calculating a root mean square value of said stroke volume variability signal over a moving or a fixed time window for obtaining the stroke volume variability value; and
    low pass filtering a signal obtained by calculating an absolute value of change of stroke volume between two consecutive stroke volume samples for obtaining a low pass filtered stroke volume variability value.

6. The method according to claim 1, further comprising:
    detecting absence of normal or deep breath by using said stroke volume variability value, and detecting a sleep phenomenon by using said absence of normal or deep breath as a discriminating parameter.

7. The method according to claim 1, further comprising:
    calculating a respiration rate value indicating respiration rhythm and depth of the subject; and
    detecting absence of normal or deep breath by using said respiration rate value, and detecting a sleep phenomenon by using said detected absence of normal or deep breath as a discriminating parameter.

8. The method according to claim 1, wherein said ballistocardiologic signal is received from the ballistocardiographic device, wherein the ballistocardiographic device is attached to a bed structure.

9. The method according to claim 8, wherein said ballistocardiographic device uses an accelerometer or an angular rate sensor configured to detect the ballistocardiologic signal of the subject.

10. The method according to claim 1, wherein said method is used for detecting a sleep disorder of at least one of sleep apnea and hypopnea, and said sleep disorder is recognized by detecting an increase in very low frequency heart rate variability, detecting no stroke volume variability, and detecting absence of normal or deep breath.

11. The method according to claim 1, further comprising:
calculating a recovery index by low pass filtering said heart rate variability ratio signal.

12. A sleep disorder monitoring system, comprising:
a ballistocardiographic detection means configured to obtain a ballistocardiologic signal of a subject;
processing means configured:
to process said ballistocardiologic signal for obtaining simultaneously a stroke volume variability signal, a high frequency heart rate variability signal, a low frequency heart rate variability signal and a very low frequency heart rate variability signal;
to obtain a low frequency heart rate variability value representing a characteristic of the low frequency heart rate variability signal;
to obtain a very low frequency heart rate variability value representing a characteristic of the very low frequency heart rate variability signal;
to obtain a stroke volume variability value representing a characteristic of the stroke volume variability signal;
to obtain a high frequency heart rate variability value representing a characteristic of the high frequency heart rate variability signal;
to obtain a respiration depth free high frequency heart rate variability value by dividing the high frequency heart rate variability value with the stroke volume variability value;
to obtain a heart rate variability ratio by dividing the respiration depth free high frequency heart rate variability value with the low frequency heart rate variability value;
to detect at least one sleep cycle from the heart rate variability ratio;
to detect a currently occurring sleep phenomenon using said heart rate variability ratio; and
to detect a sleep disorder if the very low frequency heart rate variability value during the detected sleep phenomenon is higher than a predefined reference value; and
interface means for providing a user interface towards a user, wherein the interface means is configured to output an indication of the detected sleep disorder.

13. The sleep disorder monitoring system according to claim 12, wherein said processing means is further configured to:
calculate a first derivative of at least one of the low frequency heart rate variability signal and the very low frequency heart rate variability signal, for obtaining a rate of change of the respective at least one of said low frequency heart rate variability signal and said very low frequency heart rate variability signal, and
use said rate of change of the respective one of said low frequency heart rate variability signal and said very low frequency heart rate variability signal as the respective one of the low frequency heart rate variability value and the very low frequency heart rate variability signal.

14. The sleep disorder monitoring system according to claim 12, wherein said processing means is further configured:
to calculate an average value of a rate of change of the respective of said low frequency heart rate variability signal and said very low frequency heart rate variability signal over a period of time; and
to use said average value of the rate of change of the respective of said low frequency heart rate variability signal and very low frequency heart rate variability signal as the respective one of the low frequency heart rate variability value and the very low frequency heart rate variability value.

15. The sleep disorder monitoring system according to claim 13, wherein the processing means further comprises a low pass filter configured to filter said calculated rate of change or an average value of rate of change of the respective at least one of said low frequency heart rate variability signal and very low frequency heart rate variability signal, wherein delay effects caused by said filtering on the output signal are reduced by producing an output signal combining the filtered signal with the output signal at a preceding time period, and wherein a resulting combined signal is used as the respective one of the low frequency heart rate variability value and the very low frequency the heart rate variability value.

16. The sleep disorder monitoring system according to claim 12, wherein said obtaining said stroke volume variability value comprises at least one of:
calculating a root mean square value of said stroke volume variability signal over a moving or a fixed time window for obtaining the stroke volume variability value; and
low pass filtering a signal obtained by calculating absolute value of change of stroke volume between two consecutive stroke volume samples for obtaining a low pass filtered stroke volume variability value.

17. The sleep disorder monitoring system according to claim 12, wherein said processing means is configured to detect absence of normal or deep breath by using said stroke volume variability value, and to detect a sleep phenomenon by using said absence of normal or deep breath as a discriminating parameter.

18. The sleep disorder monitoring system according to claim 12, wherein said processing means is further configured:
to calculate a respiration rate value indicating respiration rhythm and depth of the subject; and
to detect absence of normal or deep breath by using said respiration rate value, and to detect a sleep phenomenon by using said detected absence of normal or deep breath as a discriminating parameter.

19. The sleep disorder monitoring system according to claim 12, wherein said detection means comprises a ballistocardiographic device attached to a bed structure.

20. The sleep disorder monitoring system according to claim 19, wherein said ballistocardiographic device comprises an accelerometer or an angular rate sensor configured to detect said ballistocardiologic signal of the subject.

21. The sleep disorder monitoring system according to claim 12, wherein said system is configured to detect a sleep disorder of at least one of sleep apnea or hypopnea, and said sleep disorder is recognized by detecting an increase in very low frequency heart rate variability, detecting no stroke volume variability, and detecting absence of normal or deep breath.

22. The sleep disorder monitoring system according to claim 12, wherein:
   said processing means is further configured to calculate a recovery index by low pass filtering said heart rate variability ratio signal.

23. A computer program embodied on a non-transitory computer-readable medium having instructions stored thereon that, when executed by a computing device or a data-processing system, cause the computing device or the data-processing system to perform the method according to claim 1.

* * * * *